United States Patent
Tournilhac et al.

(10) Patent No.: US 6,793,940 B2
(45) Date of Patent: Sep. 21, 2004

(54) MASCARA COMPRISING A PARTICLE DISPERSION

(75) Inventors: Florence Tournilhac, Paris (FR); Frédéric Auguste, Chevilly-Larue (FR)

(73) Assignee: L'Oreal S.A., Paris (FR)

(*) Notice: Subject to any disclaimer, the term of this patent is extended or adjusted under 35 U.S.C. 154(b) by 35 days.

(21) Appl. No.: 10/195,314

(22) Filed: Jul. 16, 2002

(65) Prior Publication Data

US 2003/0064045 A1 Apr. 3, 2003

Related U.S. Application Data

(60) Provisional application No. 60/306,407, filed on Jul. 20, 2001.

(30) Foreign Application Priority Data

Jul. 16, 2001 (FR) .......................... 01 09500

(51) Int. Cl.$^7$ .............................. A61K 7/02
(52) U.S. Cl. ...................... 424/707; 424/401
(58) Field of Search ................. 424/707, 401

(56) References Cited

U.S. PATENT DOCUMENTS

| | | |
|---|---|---|
| 5,851,517 A | 12/1998 | Mougin et al. |
| 5,858,338 A | 1/1999 | Piot et al. |
| 5,945,095 A | 8/1999 | Mougin et al. |
| 6,254,877 B1 | 7/2001 | De La Poterie et al. |

FOREIGN PATENT DOCUMENTS

| | | |
|---|---|---|
| EP | 0 557 196 | 8/1993 |
| EP | 0 749 746 | 12/1996 |
| EP | 0 749 747 | 12/1996 |
| EP | 0 930 060 | 7/1999 |

OTHER PUBLICATIONS

Patent Abstracts of Japan, vol. 016, No. 342, Jul. 24, 1992, JP 04 103510.

Masakazu Hirose et al., "The structure and properties of acrylic–polyurthane hybrid emulsions," Progress in Organic Coatings, vol. 38, 2000, pp. 27–34.

"Encyclopedia of Chemical Technology," Kirk Othmr, Third Edition, vol. 22, John Wiley & Sons, 1979, pp. 332–432.

English language Derwent Abstract of EP 0 847 752, Jun. 17, 1998.

English language Derwent Abstract of EP 0 923 928, Jun. 23, 1999.

English language Derwent Abstract of EP 1 048 282, Nov. 2, 2000.

English language Derwent Abstract of EP 1 064 919, Jan. 3, 2001.

English language Derwent Abstract of EP 1 082 953, Mar. 14, 2001.

English language Derwent Abstract of FR 2 262 303, Sep. 19, 1975.

English language Derwent Abstract of FR 2 792 190, Oct. 20, 2000.

*Primary Examiner*—Jyosthna Venkat
(74) *Attorney, Agent, or Firm*—Finnegan, Henderson, Farabow, Garrett & Dunner, LLP

(57) ABSTRACT

The invention relates to a cosmetic composition for coating keratin fibers, comprising a dispersion of particles in a cosmetically acceptable medium, the particles comprising at least one at least external supple phase, comprising at least one supple polymer having a glass transition temperature of less than or equal to 60° C. and at least one at least internal rigid phase, which is an amorphous material having a glass transition temperature of greater than 60° C., the supple polymer being at least partially attached by chemical grafting onto the rigid phase.

The invention also relates to a process for coating keratin fibers, comprising the application of the composition to the keratin fibers.

The composition rapidly gives a makeup with good eyelash curling properties.

107 Claims, No Drawings

MASCARA COMPRISING A PARTICLE DISPERSION

This application claims the benefit of Provisional Application No. 60/306,407 filed Jul. 20, 2001.

The present invention relates to a composition for coating keratin fibers comprising comprising at least one dispersion of multiphase particules. The invention also relates to the use of this composition for making up keratin fibers, as well as to a process for making up these fibers. The composition and the makeup process according to the invention are more particularly intended for substantially longilinear human keratin fibers such as the eyelashes, the eyebrows and the hair, including false eyelashes and hairpieces. The composition can be a makeup composition, a makeup base, a composition to be applied to a makeup, also known as a top-coat, or alternatively a composition for cosmetically treating keratin fibers. More especially, the invention relates to a mascara.

Compositions for coating the eyelashes, known as mascara, generally comprise, in a known manner, at least one wax and at least one film-forming polymer to deposit a makeup film on the eyelashes and coat them, for example as described in document WO-A-95/15741. Users expect these products to have good cosmetic properties, such as adhesion to the eyelashes, lengthening or curling of the eyelashes, or alternatively good staying power of the mascara over time, in particular good resistance to rubbing, for example with the fingers or fabrics (handkerchiefs, towels). However, mascara compositions do not always allow good curling of the eyelashes to be obtained.

The aim of the present invention is to provide a composition for making up keratin fibers, and in particular the eyelashes, which applies easily and gives good curling of the keratin fibers.

It has been discovered that such a composition can be obtained by using a particle dispersion of particular multiphase particles, in a cosmetically acceptable medium.

The composition according to the invention applies easily and attaches well to keratin fibers such as the eyelashes. It is found that the eyelashes are curled quickly and easily after applying the composition thereto. The makeup is comfortable for the user to wear. The makeup is easily removed with standard makeup removers.

More specifically, a subject of the invention is a composition for coating keratin fibers, comprising a dispersion of multiphase particles in a cosmetically acceptable medium, the multiphase particles comprising at least one supple phase at least on the outside, comprising at least one supple polymer having at least one glass transition temperature of less than or equal to 60° C. and at least one rigid phase at least on the inside, the rigid phase being an amorphous material having at least one glass transition temperature of greater than 60° C., the supple polymer being at least partially attached by chemical grafting onto the rigid phase.

A subject of the invention is also a process for coating keratin fibers, especially the eyelashes, comprising the application to the keratin fibers of a composition as defined above.

A subject of the invention is also the use of a composition as defined above for curling the eyelashes.

A subject of the invention is also the use, in a mascara composition, of a dispersion of multiphase particles comprising at least one supple phase at least on the inside, comprising at least one supple polymer having at least one glass transition temperature of less than or equal to 60° C., and at least one rigid phase at least on the outside, the rigid phase being an amorphous material having at least one glass transition temperature of greater than 60° C., the supple polymer being at least partially attached by chemical grafting onto the rigid phase, the multiphase particles being dispersed in a cosmetically acceptable medium, to curl the eyelashes.

The glass transition temperature corresponds to the temperature at which the amorphous material changes from a glassy solid state to a rubbery state. This temperature may be measured by differential thermal analysis (DTA) and differential calorimetry ("DSC" method, for "Differential Scanning Calorimetry"). In particular, the glass transition temperature may be measured by differential calorimetry (DSC) according to ASTM standard D3418-97.

The expression "cosmetically acceptable medium" means a medium that is compatible with keratin materials, for instance human skin.

The particles according to the invention, also known as multiphase particles (or composites), are particles comprising at least one supple phase and at least one rigid phase.

The supple polymer of the particles in dispersion has at least one glass transition temperature of less than or equal to 60° C., especially ranging from −120° C. to 60° C., preferably less than or equal to 45° C,. especially ranging from −120° C. to 45° C. and preferentially less than or equal to 30° C., especially ranging from −120° C. to 30° C.

The supple polymer may be chosen from block polymers and/or random polymers. The expression "block polymers and/or random polymers" means polymers whose monomer distribution on the main chain or pendent chain members is in block and/or random form.

The supple polymer may be chosen from free-radical polymers, polycondensates and silicone polymers. The supple polymer may be chosen from polyacrylics, polymethacrylics, polyamides, polyurethanes, polyolefins, especially polyisoprenes, polybutadienes and polyisobutylenes (PIB), polyesters, polyvinyl ethers, polyvinylthio ethers, polyoxides, polysiloxanes and especially polydimethylsiloxanes (PDMS), and combinations thereof. The term "combinations" means copolymers that may be formed from monomers, leading to the formation of said polymers.

Preferably, the supple polymer may be chosen from poly(meth)acrylics, polyurethanes, polyolefins and polysiloxanes.

The amorphous material of the rigid phase has a glass transition temperature of greater than 60° C., especially greater than 60° C. and less than or equal to 200° C., preferably greater than or equal to 70° C., especially ranging from 70° C. to 200° C., in particular ranging from 70° C. to 150° C., and preferentially greater than or equal to 90° C., especially ranging from 90° C. to 150° C.

The amorphous material of the rigid phase may be a polymer, especially a block and/or random polymer. It may be a polymer chosen from polyacrylics, polymethacrylics such as, for example, poly((meth)acrylic acid), poly(meth)acrylamides, polyvinyls, polyvinyl esters, polyolfeins, polystyrenes, polyvinyl halides, for instance polyvinyl chloride (PVC), polyvinylnitriles, polyurethanes, polyesters, polyamides, polycarbonates, polysulfones, polysulfonamides, polycyclics containing a carbon-based ring in the main chain, for instance polyphenylenes or polyoxyphenylenes, and combinations thereof.

Preferably, the amorphous material of the rigid phase may be a polymer chosen from polyacrylics, polymethacrylics such as, for example, poly((meth)acrylic acid), poly (meth)acrylamides, polyvinyls, polyvinyl esters, polyolefins, polystyrenes, polyvinyl halides, for instance polyvinyl chloride (PVC), polyvinylnitriles, polyurethanes, polyamides and polyesters.

According to one preferred embodiment of the invention, the supple and rigid phases of the multiphase particles may comprise at least one free-radical polymer obtained by, or even essentially by, polymerization of monomers chosen from the group formed by:

(meth)acrylic acid esters, for instance alkyl (meth) acrylates, especially containing a $C_1$–$C_8$ alkyl group, vinyl esters of linear or branched carboxylic acids, such as vinyl acetate or vinyl stearate, styrene and its derivatives, such as chloromethylstyrene or α-methylstyrene, conjugated dienes, such as butadiene or isoprene, acrylamide, methacrylamide and acrylonitrile, vinyl chloride, (meth)acrylic acid.

The selection of monomers (nature and content), which may be a single monomer or a mixture of at least two monomers, of the supple polymer and of the amorphous material of the rigid phase, is determined by the glass transition temperature that it is desired to give to each polymer.

The polymers of the rigid and/or supple phases may be crosslinked with monomers containing at least two copolymerizable double bonds, chosen, for example, from:

conjugated dienes, such as butadiene or isoprene;

allylic esters of α,β-unsaturated carboxylic acids, such as allyl acrylate or allyl methacrylate;

allylic esters of α,β-unsaturated dicarboxylic acids, such as diallyl maleate;

polyacrylics or polymethacrylics generally comprising at least two ethylenic unsaturations, such as ethylene glycol dimethacrylate, 1,3-butylene glycol dimethacrylate, 1,4-butanediol diacrylate or pentaerythritol tetraacrylate;

polyvinyls such as divinylbenzene or trivinylbenzene;

polyallylics such as triallyl cyanurate.

Said chemical grafting allows, by the formation of covalent bonds, stable bonding of the rigid phase and the supple phase of the multiphase particles.

The chemical grafting may be performed by block free-radical polymerization (also known as block polymerization) according to the procedures that are well known to those skilled in the art. The block polymerization consists, in a first step, in polymerizing the monomers of the rigid polymer (polymer forming the rigid phase of the particles) and then, in a second step, in continuing the polymerization with the monomers forming the supple polymer (polymer forming the supple phase of the particles). In this way, the polymer chains of the supple phase are at least partially linked by covalent bonding to the chains of the polymer of the rigid phase, the covalent bonding resulting from the polymerization of a monomer of the supple polymer with a monomer of the rigid polymer. Preferentially, the monomers of the polymer of the external supple phase have greater affinity for the dispersion medium than the monomers of the polymer of the internal rigid phase.

The supple polymer may be grafted onto the rigid polymer by means of a grafting monomer, said monomer possibly being a monomer containing several double bonds (ethylenic bonds), in particular a monomer containing two ethylenic double bonds. The grafting monomer may be a conjugated diene such as those described above or an allylic ester (especially diester) of α,β-unsaturated dicarboxylic acids such as those described above (such as, for example, diallyl maleate) which contain two polymerizable functions (ethylenic double bond) of different reactivity: one of the polymerizable functions (ethylenic double bond) of the grafting monomer is polymerized with the polymer of the amorphous material of the rigid phase (rigid polymer) and the other polymerizable function (ethylenic double bond) of the same grafting monomer is polymerized with the supple polymer.

When the supple polymer or the polymer of the rigid phase is a polycondensate, it is preferred to use a polycondensate containing at least one ethylenic unsaturation capable of reacting with a monomer also comprising an ethylenic unsaturation, to form a covalent bond with the polycondensate. Polycondensates comprising one or more ethylenic unsaturations are especially obtained by polycondensation of monomers such as allyl alcohol, vinylamine or fumaric acid. For example, vinyl monomers may be polymerized with a polyurethane containing vinyl groups in or at the end of the polyurethane chain, and may thus graft a vinyl polymer onto a polyurethane; a dispersion of particles of such a grafted polymer is especially described in the publications "The structure and properties of acrylic-polyurethane hybrid emulsions", Hiroze M., Progress in Organic Coatings, 38 (2000), pages 27–34; "Survey of the applications, properties, and technology of crosslinking emulsions", Bufkin B, Journal of Coatings technology, vol. 50, No. 647, December 1978.

The same grafting principle applies to silicones using silicones comprising vinyl groups, allowing vinyl monomers to be polymerized on the silicone and thus allowing vinyl polymer chains to be grafted onto a silicone.

In one embodiment of the invention, the multiphase particles containing rigid and supple phases are film-forming, and may have a minimum film-forming temperature (MFFT) of less than or equal to about 30° C. (especially ranging from –120° C. to 30° C.), preferably less than or equal to about 25° C. (especially ranging from –120° C. to 25° C.); the particles containing rigid and supple phases may thus form a film at a temperature of about 30° C. In particular, the multiphase particles are capable of adhering to keratin materials, i.e. they are capable of remaining attached to keratin materials, especially to the eyelashes.

The particles containing rigid and supple phases generally have a size ranging from 1 nm to 10 μm and preferably ranging from 10 nm to 1 μm. The particle size may be measured, for example, using a Brookhaven BI-90 machine by the technique of light scattering, or with a Malvern Mastersizer 2000 granulometer, or alternatively by electron microscopy.

The supple phase may be present in the multiphase particles in a content of at least 10% by volume, relative to the total volume of the particle, especially ranging from 10% to 90% by volume, and preferably of at least 25% by volume, especially ranging from 25% to 90% by volume.

In any case, the rigid phase and the supple phase are incompatible, i.e. they can be distinguished using the techniques that are well known to those skilled in the art, such as, for example, the technique of observation by electron microscopy or the measurement of several glass transitions of the particles by differential calorimetry. The multiphase particles are thus inhomogeneous particles.

The morphology of the supple and rigid phases of the dispersed particles may be, for example, of core-shell type, with shell portions completely surrounding the core, but also of core-shell type with a plurality of cores, or an interpenetrating network of phases. In the multiphase particles, the supple phase is at least partly and preferably predominantly external, and the rigid phase is at least partly and preferably predominantly internal.

The multiphase particles may be prepared by consecutive series of polymerization, with different types of monomers. The particles of a first family of monomers are generally prepared in a separate step, or formed in situ by polymerization. Next, or at the same time, at least one other family of other monomers are polymerized during at least one additional polymerization step. The particles thus formed have at least one at least internal structure, or core, and at least one at least external structure, or shell. The formation of a "multilayer" heterogeneous structure is thus possible. A wide variety of morphologies may flow therefrom, of the core-shell type, but also, for example, with fragmented inclusions of the rigid phase in the supple phase. According to the invention, it is essential for the structure as an at least external supple phase to be more supple than the structure as an at least internal rigid phase.

The multiphase particles present in the composition according to the invention are in dispersion in a physiologically acceptable medium.

According to a first embodiment of the invention, the multiphase particles may be dispersed in an aqueous medium, especially a hydrophilic medium. The aqueous medium may consist predominantly of water, and preferably virtually totally of water. These dispersed particles thus form an aqueous polymer dispersion, generally known as a latex or pseudolatex. The term "latex" means an aqueous dispersion of polymer particles as may be obtained by emulsion polymerization of at least one monomer.

The dispersion of multiphase particles is generally prepared by at least one emulsion polymerization, in an essentially aqueous continuous phase, using reaction initiators, such as photochemical or thermal initiators for a free-radical polymerization, optionally in the presence of additives such as stabilizers, chain-transfer agents and/or catalysts.

The aqueous medium of the composition may comprise or may consist essentially of water, and optionally of a water-miscible solvent (mixture capable of forming at 25° C. a homogeneous mixture that is transparent to the eye), for instance lower monoalcohols containing from 1 to 5 carbon atoms, such as ethanol or isopropanol, glycols containing from 2 to 8 carbon atoms, such as propylene glycol, ethylene glycol, 1,3-butylene glycol or dipropylene glycol, $C_3$–$C_4$ ketones and $C_2$–$C_4$ aldehydes, and mixtures thereof.

The water, and optionally the water-miscible organic solvent, may be present in a content ranging from 1% to 95%, preferably from 5% to 80% and better still from 10% to 60% by weight relative to the total weight of the composition.

According to a second embodiment of the invention, the multiphase particles may be dispersed in a lipophilic medium, i.e. a nonaqueous medium, especially a nonaqueous medium that is liquid at room temperature (25° C.) and atmospheric pressure.

In this case, the particles are generally prepared by at least one solution polymerization, in a solvent or organic medium, using reaction initiators, such as free-radical thermal initiators, for an essentially free-radical polymerization. The chosen solvent phase must allow the monomers to be dissolved but it must no longer be a solvent for the final polymer, which ends up in dispersion. The compounds generally present for such a preparation may be stabilizers, chain-transfer agents and/or catalysts.

The composition, and especially the lipophilic medium, may comprise at least one volatile oil or one volatile organic solvent. Such a component evaporates during the drying of the composition according to the invention.

For the purposes of the invention, the expression "volatile oil or volatile organic solvent" means volatile organic solvents and volatile cosmetic oils, that are liquid at room temperature, having a nonzero vapor pressure, at room temperature and atmospheric pressure, ranging in particular from $10^{-2}$ to 300 mmHg (1.33 Pa to 40 000 Pa) and preferably greater than 0.3 mmHg (30 Pa). The expression "nonvolatile oil" means an oil especially having a vapor pressure of less than $10^{-2}$ mmHg (1.33 Pa).

These oils may be hydrocarbon-based oils, silicone oils or fluoro oils, or mixtures thereof.

The expression "hydrocarbon-based oil" means an oil mainly containing hydrogen and carbon atoms and optionally oxygen, nitrogen, sulfur or phosphorus atoms. The volatile hydrocarbon-based oils may be chosen from hydrocarbon-based oils containing from 8 to 16 carbon atoms, and especially $C_8$–$C_{16}$ branched alkanes, for instance $C_8$–$C_{16}$ isoalkanes of petroleum origin (also known as isoparaffins), for instance isododecane (also known as 2,2,4,4,6-pentamethylheptane), isodecane and isohexadecane, and, for example, the oils sold under the trade names Isopars or Permetyls, $C_8$–$C_{16}$ branched esters, isohexyl neopentanoate, and mixtures thereof. Other volatile hydrocarbon-based oils, for instance petroleum distillates, especially those sold under the name Shell Solt by the company Shell, may also be used. The volatile solvent is preferably chosen from hydrocarbon-based volatile oils containing from 8 to 16 carbon atoms, and mixtures thereof.

Volatile oils which may also be used are volatile silicones such as, for example, linear or cyclic volatile silicone oils, especially those with a viscosity $\leq 8$ centistokes ($8 \times 10^{-6}$ m$^2$/s) and especially containing from 2 to 7 silicon atoms, these silicones optionally comprising alkyl or alkoxy groups containing from 1 to 10 carbon atoms. As volatile silicone oils which may be used in the invention, mention may be made in particular of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Volatile fluoro solvents such as 1,1,1,2,2,3,4,5,5,5-decafluoropentane or perfluoromethylcyclopentane may also be used.

The volatile oil or volatile organic solvent may be present in the composition according to the invention in an amount ranging from 1% to 95% by weight relative to the total weight of the composition and preferably from 1% to 65% by weight.

The composition can also comprise at least one non-volatile oil chosen in particular from non-volatile hydrocarbon-based and/or silicone and/or fluoro oils.

Non-volatile hydrocarbon-based oils which may be mentioned in particular are:

hydrocarbon-based plant oils such as triglycerides consisting of fatty acid esters and of glycerol in which the fatty acids may have varied chain lengths from $C_4$ to $C_{24}$, these chains possibly being linear or branched, and saturated or unsaturated; these oils are, in particular, wheat germ oil, sunflower oil, grape seed oil, sesame oil, corn oil, apricot oil, castor oil, karite butter, avocado oil, olive oil, soybean oil, sweet almond oil, palm oil, rapeseed oil, cotton oil, hazelnut oil, macadamia oil, jojoba oil, alfalfa oil, poppy oil, pumpkin oil, sesame oil, marrow oil, rapeseed oil, blackcurrant seed oil, evening primrose oil, millet oil, barley oil, quinoa oil, rye oil, safflower oil, candlenut oil, passion flower oil and musk rose oil; or alternatively caprylic/capric acid triglycerides such as those sold by Stearineries Dubois or those sold under the names Miglyol 810, 812 and 818 by Dynamit Nobel;

synthetic ethers containing from 10 to 40 carbon atoms;

linear or branched hydrocarbons of mineral or synthetic origin, such as petroleum jelly, polydecenes, hydrogenated polyisobutene such as parleam, and squalane;

synthetic esters such as oils of formula $R_1COOR_2$ in which $R_1$ represents a linear or branched fatty acid residue containing from 1 to 40 carbon atoms and $R_2$ represents an in particular branched hydrocarbon-based chain containing from 1 to 40 carbon atoms, on condition that $R_5+R_6$ is ∃ 10, such as, for example, purcellin oil (cetostearyl octanoate), isopropyl myristate, isopropyl palmitate, $C_{12}$–$C_{15}$ alkyl benzoate, hexyl laurate, diisopropyl adipate, isononyl isononanoate, 2-ethylhexyl palmitate, isostearyl isostearate, alkyl or polyalkyl octanoates, decanoates or ricinoleates such as propylene glycol dioctanoate; hydroxylated esters such as isostearyl lactate and diisostearyl malate; and pentaerythritol esters;

fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

higher fatty acids such as oleic acid, linoleic acid or linolenic acid;

dicaprylyl carbonate sold under the tradename Cetiol CC by Cognis;

and mixtures thereof.

The non-volatile silicone oils which may be used in the composition according to the invention may be non-volatile polydimethylsiloxanes (PDMSs), polydimethylsiloxanes comprising alkyl or alkoxy groups, that are pendent and/or at the end of a silicone chain, the groups each containing from 2 to 24 carbon atoms, phenylsilicones, for instance phenyltrimethicones, phenyldimethicones, phenyltrimethylsiloxydiphenylsiloxanes, diphenyldimethicones, diphenylmethyldiphenyltrisiloxanes and 2-phenylethyl trimethylsiloxysilicates; and mixtures thereof.

The fluoro oils which may be used in the invention are, in particular, fluorosilicone oils, fluoropolyethers or fluorosilicones, as described in document EP-A-847 752.

The non-volatile oils may be present in the composition according to the invention in a content ranging from 0.1% to 80% by weight, preferably from 0.1% to 50% by weight, relative to the total weight of the composition, and better still from 0.1% to 20% by weight.

The particles containing rigid and supple phases may be present in the composition in a content ranging from 0.1% to 70% by weight of particle solids, relative to the total weight of the composition, preferably ranging from 0.5% to 55% by weight and preferentially ranging from 1% to 40% by weight.

The composition according to the invention may comprise additional solid particles, other than the multiphase particles described above. The presence of the additional solid particles advantageously allows an increase in the curling of the eyelashes imparted by the composition according to the invention.

The expression "solid particles" means particles that are in solid form at 25° C.

The additional solid particles are chosen from:

first additional particles comprising a material, known as the first material, which is a crystalline or semicrystalline solid at 25° C. with a first-order phase transition temperature, of melting or of combustion, of greater than 100° C.;

second additional solid particles comprising an amorphous material with a glass transition temperature of greater than or equal to 60° C.;

third additional solid particles comprising a wax with a hardness ranging from 6.5 MPa to 20 MPa.

The additional particles may comprise solid particles, known as first additional particles, comprising (in particular formed from) a material, known as the first material, which is a crystalline or semicrystalline solid at 25° C. with a first-order phase transition temperature, of melting or of combustion, of greater than 100° C., preferably greater than 120° C. and better still greater than 150° C.

The melting or combustion point of the first material may be measured according to ASTM standard E794-98.

For the purposes of the invention, the expression "semicrystalline material" means a material, especially a polymer, comprising a crystallizable portion and an amorphous portion with a first-order reversible temperature of change in phase, in particular of melting (solid-liquid transition).

Advantageously, the first crystalline or semicrystalline material of the first additional solid particles has a Vickers hardness of greater than or equal to 10, especially ranging from 10 to 7 500, preferably greater than or equal to 200, especially ranging from 200 to 7 500, and better still greater than or equal to 400, especially ranging from 400 to 7 500.

The Vickers hardness (HV) is determined by applying to the material a penetrometer in the form of a square-based pyramid, using a load P. The average size of a diagonal of the square imprint obtained is then measured with the penetrometer. The Vickers hardness (HV) is then calculated by the relationship:

$$HV = \frac{1854.4 \times P}{d^2} \quad \begin{array}{l} d = \text{average diagonal in } \mu m \\ P = \text{load applied, in g} \end{array}$$

The measurement of the Vickers hardness may be carried out using the M 400 g 2 microdurometer from the company LECO.

The first crystalline or semicrystalline material of said first additional solid particles may be a mineral material that may be chosen from silica, glass, diamond, copper, boron nitride, ceramics, metal oxides, especially iron oxides, for instance black iron oxide, red iron oxide or yellow iron oxide, titanium oxides and alumina, and mixtures thereof.

Said first additional solid particles may be bulk-solid particles or hollow particles. For example, the hollow silica sold under the name "Sunsil-130" by the company Sunjin Chemical may be used.

According to a first embodiment of the composition according to the invention, said first additional solid particles are formed essentially from said first crystalline or semicrystalline material defined above.

According to a second embodiment of the composition according to the invention, said first additional solid particles comprise, or even are formed essentially from, at least two different first crystalline or semicrystalline materials. This is the case, for example, for micas coated with titanium oxide or with iron oxide.

According to a third embodiment of the composition according to the invention, said first additional solid particles comprise at least said first crystalline or semicrystalline material, and at least one additional material, other than said first material, said first material forming the surface of said first particles. For these solid particles, said first material having the characteristics described above is found at the surface of said first particles, said particles comprising an additional material coated with the first material.

Advantageously, said first additional solid particles may have an average size ranging from 5 nm to 50 µm and preferably from 20 nm to 50 µm.

The additional solid particles may comprise solid particles, known as second additional solid particles, comprising an amorphous material, in particular a polymer, with a glass transition temperature of greater than or equal to 60° C. (especially ranging from 60° C. to 800° C.), advantageously greater than or equal to 80° C. (especially ranging from 80° C. to 700° C.) and preferably greater than or equal to 100° C. (especially ranging from 100° C. to 500° C.). The glass transition temperature may be measured by DSC (Differential Scanning Calorimetry) according to ASTM standard D3418-97.

Amorphous materials that may be used include non-film-forming polymers with a glass transition temperature as described above. The expression "non-film-forming polymer" means a polymer not capable by itself of forming a continuous film that adheres to a support, especially to keratin materials, at a temperature below 40° C.

Free-radical polymers or polycondensates with a glass transition temperature of greater than or equal to 60° C. may be used as amorphous polymer having this defined glass transition temperature.

Free-radical polymers that may be mentioned include:
homopolymers or copolymers of ethylene, especially of cycloethylene or of naphthylethylene;
homopolymers or copolymers of propylene, especially of hexafluoropropylene;
acrylic homopolymers or copolymers, especially polymers of acrylic acid, of dimethyladamanthyl acrylate or of chloroacrylate;
acrylamide homopolymers or copolymers;
(meth)acrylonitrile homopolymers or copolymers;
homopolymers or copolymers of acetylstyrene, of carboxystyrene or of chloromethylstyrene.

Polycondensates that may be mentioned include polycarbonates, polyurethanes, polyesters, polyamides, for instance nylon-3, polysulfones, polysulfonamides, and carbohydrates, for instance amylose triacetate.

The second additional solid particles may have an average size ranging from 10 nm to 50 µm and preferably ranging from 20 nm to 1 µm.

Additional second particles that may be used include aqueous dispersions of non-film-forming polymer sold under the names "Joncryl® SCX 8082", "Joncryl® 90" by the company Johnson Polymer, "Neocryl® XK 52" by the company Avecia Resins, and "Rhodopas® 5051" by the company Rhodia Chimie.

The additional solid particles may comprise solid particles, known as third additional solid particles, comprising (in particular in the form of) a wax, known as a hard wax, having a hardness ranging from 6.5 MPa to 20 MPa and preferably ranging from 9.5 MPa to 15 MPa. Advantageously, the wax may have a hardness of greater than 10 MPa, especially ranging from 10 to 20 MPa and better still ranging from 10 to 12 MPa.

The hardness is determined by measuring the compressive force, measured at 20° C. using a texturometer sold under the name TA-XT2i by the company Rheo, equipped with a stainless-steel cylinder 2 mm in diameter travelling at measuring speed of 0.1 mm/s, and penetrating into the wax to a penetration depth of 0.3 mm. To carry out the hardness measurement, the wax is melted at a temperature equal to the melting point of the wax +20° C. The molten wax is poured into a container 30 mm in diameter and 20 mm deep. The wax is recrystallized at ambient temperature (25° C.) over 24 hours and the wax is then stored for at least 1 hour at 20° C. before carrying out the hardness measurement. The hardness value is the compressive force measured divided by the area of the texturometer cylinder in contact with the wax.

Waxes satisfying the criteria defined above that may be used include candelilla wax, hydrogenated jojoba wax, sumac wax, ceresin, octacosanyl stearate, tetracontanyl stearate, shellac wax, behenyl fumarate, bis(1,1,1-trimethylolpropane) tetrastearate sold under the name "HEST 2T-4S" by the company Heterene, bis(1,1,1-trimethylolpropane) tetrasteabehenate sold under the name Hest 2T-4B by the company Heterene, and ozokerites, for instance the product sold under the name "Ozokerite Wax SP 1020 P" by the company Strahl & Pitsch.

The wax obtained by hydrogenation of olive oil esterified with stearyl alcohol, sold under the name "Phytowax Olive 18 L 57" or the waxes obtained by hydrogenation of castor oil esterified with cetyl alcohol, sold under the name "Phytowax ricin 16L64 and 22L73", by the company Sophim may also be used. Such waxes are described in patent publication FR-A-2 792 190.

Advantageously, the hard wax is chosen from olive wax obtained by hydrogenation of olive oil esterified with stearyl alcohol, sold under the name Phytowax Olive 18 L 57 by the company Sophim, and bis(1,1,1-trimethylolpropane) tetrastearate.

The composition according to the invention may also comprise auxiliary particles other than the rigid phase of the multiphase particles and of the additional solid particles described above. These auxiliary particles are not capable of coalescing at a temperature below 40° C. and correspond to the solid particles at 25° C. of any material, other than the rigid phase of the multiphase particles and of the additional particles described above, remaining in the form of individualized particles, or possibly bonded, but which retain, in this case, their individual particle state (these bonded particles are not coalesced at a temperature below 40° C.).

All the components present in the composition according to the invention which are in the form of solid particles that do not coalesce at a temperature below 40° C. by themselves or in the presence of all the ingredients of the composition, are considered as being either multiphase particles, or additional solid particles or auxiliary solid particles according to the definitions described above.

Thus, for example, the second additional particles may be a material chosen from waxes, fillers, polymers, such as those described below, or elastomeric particles.

Advantageously, the composition according to the invention comprises a volatile fraction and a nonvolatile fraction.

The expression "nonvolatile fraction of the composition" means all the constituents present in the composition that are not volatile. The expression "volatile compound" means a compound that, taken individually, has a nonzero vapor pressure, at room temperature (25° C.) and atmospheric pressure, ranging in particular from $10^{-2}$ to 300 mmHg (1.33 Pa to 40 000 Pa) and preferably greater than 0.3 mmHg (40 Pa).

The nonvolatile fraction of the composition in fact corresponds to the mixture of constituents remaining on the eyelashes after the mascara has been applied to the eyelashes and completely dried. The nonvolatile fraction especially comprises solid particles chosen from the multiphase particles, the additional solid particles and the auxiliary solid particles described above.

Preferably, the mascara comprises solid particles chosen from the multiphase particles, the additional solid particles and the auxiliary solid particles described above in a content such that the volume fraction of said solid particles is greater than or equal to 50% (especially from 50% to 99%) and preferably greater than or equal to 60% (especially from 60% to 99%) and is more preferably greater than or equal to 70% (especially from 70% to 95%) of the total volume of the nonvolatile fraction of the composition.

The expression "volume fraction of the solid particles" means the percentage of the total volume of all the solid particles present in the composition, relative to the total volume of all the compounds of the nonvolatile fraction of the composition.

The volume fraction (VF) of solid particles present in the nonvolatile fraction of the composition is equal to the total volume of the total volume V of said particles divided by the total volume V' of the nonvolatile fraction of the composition, expressed as a percentage.

The volume V of solid particles is equal to the mass m of said solid particles in the composition divided by the density D of the particles. The density is calculated according to the method described below.

$$\text{Volume fraction: } VF=100 \times V/V' \text{ and } V=m/D$$

The total volume V' of the nonvolatile fraction of the composition is calculated by adding the volume of each nonvolatile constituent present in the composition.

Preferably, the rigid phases of the multiphase particles and the additional first particles described above are present in the composition in a content such that the volume fraction of the rigid phases of the multiphase particles and of the first additional particles is between 10% and 90% of the total volume of the fraction of solid particles, said solid particles being chosen from the multiphase particles, the additional solid particles and the auxiliary solid particles described above.

Advantageously, the composition comprises a volatile fraction and a nonvolatile fraction comprising the multiphase particles as defined above, and the rigid phases of the multiphase particles described above may be present in the composition in a content such that the volume fraction of the rigid phases of the multiphase particles may be between 0.55% and 99% of the total volume of the nonvolatile fraction of the composition, preferably between 1% and 95% and even more preferably between 10% and 70%.

The composition according to the invention may also comprise at least one wax, known as the additional wax, other than the hard wax of the third additional solid particles described above. The additional wax especially has a hardness of less than 6.5 MPa.

For the purposes of the present invention, the term "wax" means a lipophilic fatty compound that is solid at room temperature (25° C.) and atmospheric pressure (760 mmHg, i.e. 105 Pa), which undergoes a reversible solid/liquid change of state and which has a melting point of greater than 30° C. and better still greater than 55° C., which may be up to 200° C., in particular up to 120° C. By taking the wax to its melting point, it is possible to make it miscible with oils and to form a microscopically homogeneous mixture, but on returning the temperature of the mixture to room temperature, recrystallization of the wax in the oils of the mixture is obtained. According to the invention, the melting point values correspond to the melting peak measured using a differential scanning calorimeter (DSC), for example the calorimeter sold under the name DSC 30 by the company Mettler, with a temperature increase of 5 or 10° C. per minute.

For the purposes of the invention, the waxes are those generally used in cosmetics and dermatology. Mention may be made in particular of beeswax, lanolin wax, Chinese insect waxes, rice wax, carnauba wax, ouricury wax, sugar cane wax, Japan wax, montan wax, microcrystalline waxes, paraffin waxes, ceresin wax, lignite wax, polyethylene waxes and the waxes obtained by Fisher-Tropsch synthesis, and fatty acid esters and glycerides that are solid at 40° C. and better still at more than 55° C. Mention may also be made of the waxes obtained by catalytic hydrogenation of animal or plant oils containing linear or branched $C_8$–$C_{32}$ fatty chains. Among these, mention may be made in particular of hydrogenated sunflower oil, hydrogenated castor oil, hydrogenated coconut oil and hydrogenated lanolin oil. Mention may also be made of silicone waxes or fluoro waxes.

The additional wax present in the composition may be dispersed in the form of particles in an aqueous medium. These particles may have an average size ranging from 50 nm to 10 μm and preferably from 50 nm to 3.5 μm.

In particular, the additional wax may be present in the form of a wax-in-water emulsion, the waxes possibly being in the form of particles with an average size ranging from 1 μm to 10 μm and preferably from 1 μm to 3.5 μm.

In another embodiment of the composition according to the invention, the additional wax may be present in the form of a wax microdispersion, the additional wax being in the form of particles with an average size of less than 1 μm and in particular ranging from 50 nm to 500 nm. Wax microdispersions are disclosed in documents EP-A-557 196 and EP-A-1 048 282.

The composition according to the invention may comprise at least one additional film-forming polymer, in addition to the polymer of the supple phase of the multiphase particles described above.

The additional film-forming polymer may be a polymer dissolved or dispersed in the form of solid particles in an aqueous phase of the composition, or alternatively dissolved or dispersed in the form of solid particles in a liquid fatty phase of the composition. The composition may comprise a mixture of these polymers. When the additional film-forming polymer is in the form of solid particles, these particles may have an average particle size ranging from 5 nm to 600 nm and preferably from 20 nm to 300 nm.

The additional film-forming polymer may be present in the composition according to the invention in a solids content ranging from 0.1% to 60% by weight relative to the total weight of the composition, preferably from 0.5% to 20% by weight and better still from 1% to 10% by weight.

In the present patent application, the expression "film-forming polymer" means a polymer capable of forming, by itself or in the presence of an auxiliary film-forming agent, a continuous film that adheres to a support, especially to keratin materials.

A film-forming polymer capable of forming a hydrophobic film, i.e. a polymer whose film has a solubility in water at 25° C. of less than 1% by weight, is preferably used.

Among the film-forming polymers that may be used in the composition of the present invention, mention may be made of synthetic polymers, of free-radical type or of polycondensate type, and polymers of natural origin, and mixtures thereof.

The expression "free-radical film-forming polymer" means a polymer obtained by polymerization of monomers containing unsaturation, especially ethylenic unsaturation, each monomer being capable of homopolymerizing (unlike polycondensates). The film-forming polymers of free-radical type may especially be vinyl polymers or copolymers, especially (meth)acrylic polymers in acid, ester or amide form.

According to the present invention, the alkyl group of the esters may either be fluorinated, or perfluorinated, i.e. some or all of the hydrogen atoms of the alkyl group are replaced with fluorine atoms.

The film-forming vinyl polymers may also result from the homopolymerization or copolymerization of monomers chosen from vinyl esters and styrene monomers. In particular, these monomers may be polymerized with acid monomers and/or esters thereof and/or amides thereof, such as those mentioned above.

Any monomer known to those skilled in the art that falls within the categories of acrylic and vinyl monomers (including monomers modified with a silicone chain) may be used.

Among the film-forming polycondensates that may be mentioned are polyurethanes, polyesters, polyesteramides, polyamides, epoxy ester resins and polyureas.

Copolymers based on isophthalate/sulfoisophthalate, and more particularly copolymers obtained by condensation of diethylene glycol, cyclohexanedimethanol, isophthalic acid and sulfoisophthalic acid, may be used. Such polymers are sold, for example, under the brand name Eastman AQ® by the company Eastman Chemical Products.

The polymers of natural origin, optionally modified, may be chosen from shellac resin, sandarac gum, dammar resins, elemi gums, copal resins and cellulose polymers, and mixtures thereof.

According to a first embodiment of the composition according to the invention, the additional film-forming polymer may be present in the form of particles in aqueous dispersion, which is generally known as a latex or pseudolatex. The techniques for preparing these dispersions are well known to those skilled in the art.

Aqueous dispersions of film-forming polymers which may be used are the acrylic dispersions sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® by the company Dow Chemical, Daitosol 5000 AD® by the company Daito Kasey Kogyo; or the aqueous dispersions of polyurethane sold under the names Neorez R-981® and Neorez R-974® by the company Avecia-Neoresins, Avalure UR-405®, Avalure UR-410®, Avalure UR-425®, Avalure UR-450®, Sancure 875®, Sancure 861®, Sancure 878® and Sancure 2060® by the company Goodrich, Impranil 85® by the company Bayer and Aquamere H-1511® by the company Hydromer.

Aqueous dispersions of film-forming polymers which may also be used are the polymer dispersions resulting from the radical-mediated polymerization of one or more radical-mediated monomers within and/or partially at the surface of pre-existing particles of at least one polymer chosen from the group consisting of polyurethanes, polyureas, polyesters, polyesteramides and/or alkyds. These polymers are generally referred to as hybrid polymers.

According to a second embodiment of the composition according to the invention, the additional film-forming polymer may be a water-soluble polymer and is thus present in an aqueous phase of the composition in dissolved form.

Examples of water-soluble film-forming polymers which may be mentioned are:
proteins, for instance proteins of plant origin such as wheat proteins and soybean proteins; proteins of animal origin such as keratins, for example keratin hydrolysates and sulfonic keratins;
anionic, cationic, amphoteric or nonionic chitin or chitosan polymers;
polymers of celluloses such as hydroxyethylcellulose, hydroxypropylcellulose, methylcellulose, ethylhydroxyethylcellulose and carboxymethylcellulose, and quaternized cellulose derivatives;
acrylic polymers or copolymers, such as polyacrylates or polymethacrylates;
vinyl polymers, for instance polyvinylpyrrolidones, copolymers of methyl vinyl ether and of malic anhydride, the copolymer of vinyl acetate and of crotonic acid, copolymers of vinylpyrrolidone and of vinyl acetate; copolymers of vinylpyrrolidone and of caprolactam; polyvinyl alcohol;
polymers of natural origin, which are optionally modified, such as:
gum arabics, guar gum, xanthan derivatives, karaya gum;
alginates and carrageenans;
glycoaminoglycans, hyaluronic acid and derivatives thereof;
shellac resin, sandarac gum, dammar resins, elemi gums and copal resins;
deoxyribonucleic acid;
mucopolysaccharides such as hyaluronic acid and chondroitin sulfate, and mixtures thereof.

According to another embodiment of the composition according to the invention, the film-forming polymer may be present in a liquid fatty phase comprising organic solvents or oils such as those described above. For the purposes of the invention, the expression "liquid fatty phase" means a fatty phase which is liquid at room temperature (25° C.) and atmospheric pressure (760 mmHg, i.e. $10^5$ Pa), composed of one or more fatty substances that are liquid at room temperature, also known as oils, which are generally mutually compatible.

The liquid fatty phase preferably comprises a volatile oil, optionally mixed with a nonvolatile oil, the oils possibly being chosen from those mentioned above.

According to a third embodiment of the composition according to the invention, the additional film-forming polymer may be present in the form of surface-stabilized particles dispersed in a liquid fatty phase.

The dispersion of surface-stabilized polymer particles may be manufactured as disclosed in document EP-A-749 747.

The polymer particles are surface-stabilized by means of a stabilizer which may be a block polymer, a grafted polymer and/or a random polymer, alone or as a mixture.

Dispersions of film-forming polymer in the liquid fatty phase, in the presence of stabilizers, are disclosed in particular in documents EP-A-0 749 746, EP-A-0 923 928 and EP-A-0 930 060, the content of which is incorporated in the present patent application by reference.

The size of the polymer particles dispersed either in the aqueous phase or in the liquid fatty phase can range from 5 nm to 600 nm and preferably from 20 nm to 300 nm.

According to a fourth embodiment of the composition according to the invention, the additional film-forming polymer may be dissolved in the liquid fatty phase, in which case the film-forming polymer is said to be a liposoluble polymer.

Examples of liposoluble polymers which may be mentioned are copolymers of vinyl ester (the vinyl group being directly linked to the oxygen atom of the ester group and the vinyl ester containing a saturated, linear or branched hydrocarbon-based radical of 1 to 19 carbon atoms, linked to the carbonyl of the ester group) and of at least one other monomer which may be a vinyl ester (other than the vinyl ester already present), an α-olefin (containing from 8 to 28 carbon atoms), an alkyl vinyl ether (in which the alkyl group comprises from 2 to 18 carbon atoms) or an allylic or methallylic ester (containing a saturated, linear or branched hydrocarbon-based radical of 1 to 19 carbon atoms, linked to the carbonyl of the ester group).

These copolymers may be crosslinked with the aid of crosslinking agents, the aim of which is to [lacuna] which may be either of the vinyl type or of the allylic or methallylic type, such as tetraallyloxyethane, divinylbenzene, divinyl octanedioate, divinyl dodecanedioate and divinyl octadecanedioate.

Liposoluble film-forming polymers which may also be mentioned are liposoluble homopolymers, and in particular those resulting from the homopolymerization of vinyl esters containing from 9 to 22 carbon atoms or of alkyl acrylates or methacrylates, and alkyl radicals containing from 10 to 20 carbon atoms.

The liposoluble copolymers and homopolymers defined above are known and are described in particular in patent application FR-A-2 262 303; they may have a weight-average molecular weight ranging from 2 000 to 500 000 and preferably from 4 000 to 200 000.

As liposoluble film-forming polymers which may be used in the invention, mention may also be made of polyalkylenes and in particular copolymers of $C_2$–$C_{20}$ alkenes, such as polybutene, alkylcelluloses with a linear or branched, saturated or unsaturated $C_1$–$C_8$ alkyl radical, for instance ethylcellulose and propylcellulose, copolymers of vinylpyrrolidone (VP) and in particular copolymers of vinylpyrrolidone and of $C_2$ to $C_{40}$ and better still $C_3$ to $C_{20}$ alkene.

According to one preferred embodiment of the composition according to the invention, the additional film-forming polymer may be a polymer capable of forming a deposit, especially a film, producing at a concentration of 7% in water, a shrinkage of isolated stratum corneum of greater than 1% at 30° C. under a relative humidity of 40%, preferably more than 1.2% and better still of more than 1.5%. This shrinkage is measured using an extensiometer according to the method described below.

The composition according to the invention may comprise an auxiliary film-forming agent to allow the formation of a film at room temperature of the multiphase particles according to the invention or of the additional film-forming polymer. The auxiliary agent may be a coalescer or a plasticizer known to those skilled in the art. A plasticizer is generally an organic compound that remains in the composition during the formation of the film. A coalescer is generally a volatile organic compound that evaporates during the formation of the film.

The composition according to the invention can contain emulsifying surfactants present in particular in a proportion ranging from 2 to 30% by weight relative to the total weight of the composition, and better still from 5% to 15%. These surfactants can be chosen from anionic and nonionic surfactants. Reference may be made to the document "Encyclopedia of Chemical Technology, Kirk-Othmer", volume 22, pp. 333–432, 3rd edition, 1979, Wiley, for the definition of the properties and functions (emulsifying) of the surfactants, in particular pp. 347–377 of this reference, for the anionic and nonionic surfactants.

The surfactants preferably used in the composition according to the invention are chosen:

from nonionic surfactants: fatty acids, fatty alcohols, polyethoxylated or polyglycerolated fatty alcohols such as polyethoxylated stearyl or cetylstearyl alcohol, fatty acid esters of sucrose, alkyl glucose esters, in particular polyoxyethylenated fatty esters of $C_1$–C6 alkyl glucose and mixtures thereof;

from anionic surfactants: $C_{16}$–$C_{30}$ fatty acids neutralized with amines, aqueous ammonia or alkaline salts and mixtures thereof.

Surfactants which make it possible to obtain an oil-in-water or wax-in-water emulsion are preferably used.

The composition can also comprise at least one dyestuff such as pulverulent compounds, for example in a proportion of from 0.01 to 25% of the total weight of the composition. The pulverulent compounds can be chosen from the pigments and/or nacres usually used in mascaras.

The pigments can be white or colored, and inorganic and/or organic. Among the inorganic pigments which may be mentioned are titanium dioxide, which has optionally been surface-treated, zirconium oxide or cerium oxide, as well as iron oxide or chromium oxide, manganese violet, ultramarine blue, chromium hydrate and ferric blue. Among the organic pigments which may be mentioned are carbon black, pigments of D & C type, and lakes based on cochineal carmine, barium, strontium, calcium or aluminum.

The nacreous pigments can be chosen from white nacreous pigments such as mica coated with titanium or with bismuth oxychloride, colored nacreous pigments such as titanium mica with iron oxides, titanium mica with, in particular, ferric blue or chromium oxide, titanium mica with an organic pigment of the abovementioned type and nacreous pigments based on bismuth oxychloride.

The composition according to the invention may also comprise fillers that can be chosen from those which are well known to those skilled in the art and which are commonly used in cosmetic compositions. Fillers which may be used in particular are:

talc, which is a hydrated magnesium silicate used in the form of particles generally less than 40 microns, micas, which are aluminosilicates of varied compositions, present in the form of flakes from 2 to 200 microns in size, preferably from 5 to 70 microns in size, and between 0.1 and 5 microns thick, preferably from 0.2 to 3 microns thick, it being possible for these micas to be of natural origin, such as muscovite, margarite, roscoelite, lipidolite or biotite, or of synthetic origin, starch, in particular rice starch, kaolin, which is a hydrated aluminum silicate, present in the form of particles of isotropic form which are generally less than 30 microns in size, zinc oxide and titanium oxide, which are generally used in the form of particles not exceeding a few microns in size, calcium carbonate, magnesium carbonate or magnesium hydrocarbonate, microcrystalline cellulose, silica, synthetic polymer powders such as polyethylene, polyesters (polyethylene isophthalate or terephthalate), polyamides such as those sold under the trade name "Nylon" or "Teflon", and silicone powders.

The composition according to the invention can also contain ingredients commonly used in cosmetics, such as trace elements, softeners, sequestering agents, fragrances, thickeners, vitamins, proteins, ceramides, cohesion agents, basifying or acidifying agents usually used in cosmetics, emollients, preserving agents, sunscreens and antioxidants.

The composition according to the invention may be in the form of a wax-in-water, water-in-wax, oil-in-water or water-in-oil emulsion, or may be an anhydrous composition.

Needless to say, a person skilled in the art will take care to select this or these optional additional compound(s), and/or the amount thereof, such that the advantageous properties of the composition according to the invention are not, or are not substantially, adversely affected by the addition envisaged.

The composition according to the invention can be prepared according to the usual methods of the fields under consideration.

The invention is illustrated in greater detail in the example that follows.

Method for measuring the density of solid particles:

The apparent density of solid particles is measured using a Gay-Lussac pycnometer.

A precision balance (accuracy of 1 mg) is used and the measurements are carried out in a chamber thermostatically maintained at 25° C. (±0.5° C.). Two reference liquids having a density D are also used, which are demineralized water (D=1 000 kg/m$^3$) and heptane (D=683.7 kg/m$^3$). The density of the solid particles is measured with each reference liquid.

The pycnometer and the products used to carry out the measurement are placed at a temperature of 25° C. The masses given below are expressed in kilograms.

The mass M0 of the pycnometer is measured, and the pycnometer is then filled completely with the reference liquid used, avoiding the introduction of air bubbles. The mass M1 of the filled pycnometer is measured.

Next, a mixture is prepared of mass M2 of the material whose density D2 it is desired to measure with a mass M3 of reference liquid. The mixture is stirred and then, just at the end of stirring, the pycnometer is filled with this mixture and the mass M4 of the filled pycnometer is measured. The mass M4−M0 of the mixture present in the pycnometer is thus determined.

Since the pycnometer has a constant filling volume, the following relationship may thus be established: $(M1-M0)/D=(M2/D2+M3/D)\times(M4-M0)/(M2+M3)$ This relationship makes it possible to calculate the value of the density D2 of the solid particles, expressed in kg/m$^3$. A value of the density of the solid particles is thus determined for each of the reference liquids. According to the invention, the highest value (among the density measured with distilled water and the density measured with heptane) is adopted as the density value for the determination of the volume fraction of the solid particles.

Method for Measuring the Shrinkage of a Polymer:

The principle consists in measuring before treatment and after treatment the length of a specimen of isolated stratum corneum and in determining the percentage of shrinkage of the specimen.

1 cm×0.4 cm specimens of stratum corneum ranging from 10 to 20 µm thick, mounted on an MTT 610 extensiometer sold by the company Diastron, are used.

The specimen is placed between two jaws and then left for 12 hours under an atmosphere at 30° C. and 40% relative humidity.

The specimen is pulled at a speed of 2 mm/minute to a length between 5 and 10% of the initial length, to determine the length $l_1$ at and above which the specimen begins to exert a force on the jaws that is detected by the machine.

The specimen is then relaxed and 2 mg of an aqueous composition at 7% by weight of polymer are then applied to the stratum corneum. After total evaporation of the composition, the specimen is pulled under the same conditions as those described above in order also to determine the length $l_2$ for the treated specimen.

The percentage of shrinkage is determined by the ratio: $100\times(l_2-l_1)/l_1$.

EXAMPLE 1 a) A latex of core/shell structure formed from 10% by weight, relative to the total weight of polymer particles, of inner rigid phase (core) formed from 100% by weight of methyl methacrylate (weight % relative to the total weight of the rigid phase), and from 90% by weight, relative to the total weight of polymer particles, of outer supple phase formed from 50% by weight of n-butyl acrylate, 45% by weight of methyl methacrylate and 5% by weight of methacrylic acid (weight % expressed relative to the total weight of the supple phase) is prepared.

The supple phase has a glass transition temperature of about 10° C. and the rigid phase has a glass transition temperature of about 100° C. The multiphase particles comprise 10% by weight of inner rigid phase and 90% by weight of outer supple phase (weight % relative to the total weight of the polymer particles).

This latex is prepared in two sequential polymerization steps:

In a first step, the methyl methacrylate and potassium persulfate dissolved to 0.4% in water are introduced into an aqueous solution containing 4% by weight of sodium lauryl sulfate, with stirring in a reactor heated to 80° C.; the mixture is left stirring for 30 minutes. Next, sodium bisulfite is added in a sodium bisulfite/potassium persulfate weight ratio of 1/4, dissolved in a minimum amount of water. The mixture is left to react for 1 hour.

In a second step, the mixture of n-butyl acrylate, methyl methacrylate and methacrylic acid (50/45/5 weight mixture) is added to the polymer emulsion obtained at the end of the first step, over 30 minutes, followed by simultaneous addition over 5 minutes of potassium persulfate dissolved to 0.1% in water. Next, sodium bisulfite is added in an added sodium bisulfite/added potassium persulfate weight ratio equal to 1/2 and the mixture is reacted for 3 hours at 80° C., then cooled to room temperature (25° C.) and the concentration of the polymer particles is adjusted to obtain a polymer solids content of 35% by weight.

b) A mascara A having the composition below is prepared:

| | |
|---|---|
| Carnauba wax | 20 g |
| Polyoxyethylenated (30 EO) glyceryl stearate (Tagat S from the company Goldschmidt) | 8 g |
| Black iron oxide | 5 g |
| Latex according to a) | 10 gAM |
| Propylene glycol | 5 g |
| Hydroxyethylcellulose | 2.5 g |
| Preserving agents | qs |
| Water | qs 100 g |

AM Means Active Material c) A latex-free control mascara B (not in accordance with the invention) having the compostion below is prepared:

| | |
|---|---|
| Carnauba wax | 20 g |
| Polyoxyethylenated (30 EO) glyceryl stearate (Tagat S from the company Goldschmidt) | 8 g |
| Black iron oxide | 5 g |
| Propylene glycol | 5 g |
| Hydroxyethylcellulose | 2.5 g |
| Preserving agents | qs |
| Water | qs 100 g |

After depositing on the eyelashes and drying, the mascara A comprising a dispersion of multiphase particles according to the invention curls the eyelashes more than the mascara B.

What is claimed is:

1. A cosmetic composition for coating keratin fibers, comprising a dispersion of multiphase particles in a cosmetically acceptable medium, said multiphase particles comprising at least one at least partially external supple phase comprising at least one supple polymer having at least one glass transition temperature of less than or equal to 60° C. and at least one at least partially internal rigid phase, said rigid phase being an amorphous material having at least one glass transition temperature of greater than 60° C., said at least one supple polymer being at least partially attached by chemical grafting onto said rigid phase.

2. A composition according to claim 1, wherein said at least one supple polymer has a glass transition temperature ranging from −120° C. to 60° C.

3. A composition according to claim 1, wherein said at least one supple polymer has a glass transition temperature of less than or equal to 45° C.

4. A composition according to claim 1, wherein said at least one supple polymer has a glass transition temperature ranging from −120° C. to 45° C.

5. A composition according to claim 1, wherein said at least one supple polymer has a glass transition temperature of less than or equal to 30° C.

6. A composition according to claim 1, wherein said at least one supple polymer has a glass transition temperature ranging from −120° C. to 30° C.

7. A composition according to claim 1, wherein said at least one supple polymer is chosen from polyacrylics, polymethacrylics, polyamides, polyurethanes, polyolefins, polyesters, polyvinyl ethers, polyvinylthio ethers, polyoxides, and polysiloxanes.

8. A composition according to claim 1, wherein said at least one supple polymer is chosen from, polyacrylics, polymethacrylics, polyurethanes, polyolefins and polysiloxanes.

9. A composition according to claim 8, wherein said polyolefins are chosen from polyisoprenes, polybutadienes, and polyisobutylenes.

10. A composition according to claim 1, wherein said amorphous material of said rigid phase has a glass transition temperature of greater than 60° C. and less than or equal to 200° C.

11. A composition according to claim 1, wherein said amorphous material of said rigid phase has a glass transition temperature of greater than or equal to 70° C.

12. A composition according to claim 1, wherein said amorphous material of said rigid phase has a glass transition temperature ranging from 70° C. to 200° C.

13. A composition according to claim 1, wherein said amorphous material of said rigid phase has a glass transition temperature of greater than 90° C.

14. A composition according to claim 1, wherein said amorphous material of said rigid phase has a glass transition temperature ranging from 90° C. to 150° C.

15. A composition according to claim 1, wherein said amorphous material of said rigid phase is a polymer.

16. A composition according to claim 15, wherein said polymer is chosen from block and random copolymers.

17. A composition according to claim 1, wherein said amorphous material of said rigid phase is a polymer chosen from polyacrylics, polymethacrylics, poly(meth)acrylamides, polyvinyls, polyvinyl esters, polyolefins, polystyrenes, polyvinyl halides, polyvinylnitriles, polyurethanes, polyesters, polyamides, polycarbonates, polysulfones, polysulfonamides, polycyclics containing a carbon-based ring in the main chain, polyoxyphenylenes, and combinations thereof.

18. A composition according to claim 1, wherein said amorphous material of said rigid phase is a polymer chosen from polyacrylics, polymethacrylics, poly(meth)acrylamides, polyvinyls, polyvinyl esters, polyolefins, polystyrenes, polyvinyl halides, polyvinylnitriles, polyurethanes, polyamides and polyesters.

19. A composition according to claim 1, wherein said supple and rigid phases of said particles comprise at least one free-radical polymer obtained by polymerization of monomers chosen from alkyl (meth)acrylate containing a $C_1$–$C_8$ alkyl group, vinyl esters of linear or branched carboxylic acids, styrene and its derivatives, conjugated dienes, acrylamide, methacrylamide, acrylonitrile, vinyl chloride, and (meth)acrylic acid.

20. A composition according to claim 1, wherein at least one of said rigid and supple phases comprises a polymer crosslinked using a monomer containing at least two copolymerizable double bands.

21. A composition according to claim 20, wherein said polymer is crosslinked with a monomer chosen from conjugated dienes, allylic esters of α,β-unsaturated carboxylic acids, allylic esters of α,β-unsaturated dicarboxylic acids, polyacrylics or polymethacrylics generally comprising at least two ethylenic unsaturations, polyvinyls, and polyallylics.

22. A composition according to claim 21, wherein said polymer is crosslinked with a monomer chosen from butadiene, isoprene, allyl acrylate, allyl methacrylate, diallyl maleate, ethylene glycol dimethacrylate, 1,3-butylene glycol dimethacrylate, 1,4-butanediol diacrylate, pentaerythritol tetraacrylate, divinylbenzene, trivinylbenzene and triallyl cyanurate.

23. A composition according to claim 1, wherein said chemical grafting is formed by covalent bonding of said rigid phase and said supple phase of said particles.

24. A composition according to claim 1, wherein said amorphous material of said rigid phase is a polymer and said chemical grafting is performed by block free-radical polymerization.

25. A composition according to claim 1, wherein said amorphous material of said rigid phase is a polymer and said chemical grafting is performed by a grafting monomer.

26. A composition according to claim 25, wherein said grafting monomer contains two ethylenic double bonds.

27. A composition according to claim 26, wherein said grafting monomer is chosen from conjugated dienes and allylic esters of α,β-unsaturated dicarboxylic acids.

28. A composition according to claim 15, wherein said at least one supple polymer or the polymer of said rigid phase is a polycondensate containing at least one ethylenic unsaturation capable of reacting with a monomer also comprising an ethylenic unsaturation to form a covalent bond with said polycondensate.

29. A composition according to claim 28, wherein said polycondensate comprising at least one ethylenic unsaturation is obtained by polycondensation of monomers chosen from allyl alcohol, vinylamine and fumaric acid.

30. A composition according to claim 1, wherein said multiphase particles are film-forming.

31. A composition according to claim 30, wherein said multiphase particles have a minimum film-forming temperature of less than or equal to 30° C.

32. A composition according to claim 30, wherein said multiphase particles have a minimum film-forming temperature of −120° C. to 30° C.

33. A composition according to claim 1, wherein said multiphase particles are capable of adhering to keratin materials.

34. A composition according to claim 33, wherein said keratin materials are eyelashes.

35. A composition according to claim 1, wherein said multiphase particles have a size ranging from 1 nm to 10 μm.

36. A composition according to claim 1, wherein said multiphase particles have a size ranging from 10 nm to 1 μm.

37. A composition according to claim 1, wherein said supple phase is present in said multiphase particles in a content ranging from 10% to 90% by volume, relative to the total volume of the particle.

38. A composition according to claim 1, wherein said supple phase is present in said multiphase particles in a content ranging from 25% to 90% by volume, relative to the total volume of the particle.

39. A composition according to claim 1, wherein said multiphase particles are dispersed in an aqueous medium.

40. A composition according to claim 39, wherein said aqueous medium is present in a content from 1% to 95% by weight, relative to the total weight of the composition.

41. A composition according to claim 40, wherein said aqueous medium is present in a content from 5% to 80% by weight, relative to the total weight of the composition.

42. A composition according to claim 41, wherein said aqueous medium is present in a content from 10% to 60% by weight, relative to the total weight of the composition.

43. A composition according to 39, wherein said aqueous medium comprises water and, optionally, a water-miscible solvent.

44. A composition according to claim 43, wherein said water-miscible solvent is chosen from glycols containing from 2 to 8 carbon atoms, lower monoalcohols containing from 1 to 5 carbon atoms, $C_3$–$C_4$ ketones, $C_2$–$C_4$ aldehydes, and mixtures thereof.

45. A composition according to claim 43, wherein said water and, optionally, said water-miscible solvent, are present in an amount ranging from 1% to 95% by weight, relative to the total weight of the composition.

46. A composition according to claim 43, wherein said water and, optionally, said water-miscible solvent, are present in an amount ranging from 5% to 80% by weight, relative to the total weight of the composition.

47. A composition according to claim 43, wherein said water and optionally, said water-miscible solvent, are present in an amount ranging from 10% to 60% by weight, relative to the total weight of the composition.

48. A composition according to claim 1, wherein said particles are dispersed in a nonaqueous medium.

49. A composition according to claim 48, wherein said nonaqueous medium comprises at least one volatile component chosen from at least one volatile oil and at least one volatile organic solvent.

50. A composition according to claim 49, wherein said at least one volatile organic solvent is chosen from volatile fluoro solvents chosen from 1,1,1,2,2,3,4,5,5,5-decafluoropentane and perfluoromethylcyclopentane.

51. A composition according to claim 49, wherein said at least one volatile component is present in an amount ranging from 1% to 95% by weight, relative to the total weight of the composition.

52. A composition according to claim 51, wherein said at least one volatile component is present in an amount ranging from 1% to 65% by weight, relative to the total weight of the composition.

53. A composition according to claim 49, wherein said at least one volatile oil is chosen from octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane, isododecane, isodecane and isohexadecane.

54. A composition according to claim 1, wherein said composition comprises at least one nonvolatile oil.

55. A composition according to claim 54, wherein said at least one nonvolatile oil is present in an amount ranging from 0.1% to 80% by weight, relative to the total weight of the composition.

56. A composition according to claim 55, wherein said at least one nonvolatile oil is present in an amount ranging from 0.1% to 50% by weight, relative to the total weight of the composition.

57. A composition according to claim 56, wherein said at least one nonvolatile oil is present in an amount ranging from 0.1% to 20% by weight, relative to the total weight of the composition.

58. A composition according to claim 1, wherein said multiphase particles are present in an amount ranging from 0.1% to 70% by weight of particle solids, relative to the total weight of the composition.

59. A composition according to claim 58, wherein said multiphase particles are present in an amount ranging from 0.5% to 55% by weight of particle solids, relative to the total weight of the composition.

60. A composition according to claim 59, wherein said multiphase particles are present in an amount ranging from 1% to 40% by weight of particle solids, relative to the total weight of the composition.

61. A composition according to claim 1, wherein said composition further comprises additional solid particles chosen from first additional solid particles comprising a first material that is a crystalline or semicrystalline solid at 25° C. with a first-order phase transition temperature, of melting or of combustion, of greater than 100° C.;

second additional solid particles comprising an amorphous material having a glass transition temperature of greater than or equal to 60° C.; and third additional solid particles comprising a wax having a hardness ranging from 6.5 MPa to 20 MPa.

62. A composition according to claim 61, wherein said first additional solid particles comprise a first material, which is a crystalline or semicrystalline solid at 25° C. with a first-order phase transition temperature, of melting or of combustion, of greater than 100° C.

63. A composition according to claim 62, wherein said first additional solid particles comprise a first material, which is a crystalline or semicrystalline solid at 25° C. with a first-order phase transition temperature, of melting or of combustion, of greater than 120° C.

64. A composition according to claim 63, wherein said first additional solid particles comprise a first material, which is a crystalline or semicrystalline solid at 25° C. with a first-order phase transition temperature, of melting or of combustion, of greater than 150° C.

65. A composition according to claim claim 62, wherein said first crystalline or semicrystalline material has a Vickers hardness of greater than or equal to 10.

66. A composition according to claim claim 65, wherein said first crystalline or semicrystalline material has a Vickers hardness of 10 to 7 500.

67. A composition according to claim 66, wherein said first crystalline or semicrystalline material has a Vickers hardness of greater than or equal to 200.

68. A composition according to claim 67, wherein said first crystalline or semicrystalline material has a Vickers hardness of 200 to 7 500.

69. A composition according to claim 68, wherein said first crystalline or semicrystalline material has a Vickers hardness of greater than or equal to 400.

70. A composition according to claim 69, wherein said first crystalline or semicrystalline material has a Vickers hardness of 400 to 7 500.

71. A composition according to claim 62, wherein said first crystalline or semicrystalline material is chosen from silica, glass, diamond, copper, boron nitride, ceramics, metal oxides, alumina, and mixtures thereof.

72. A composition according to claim 61, wherein said additional solid particles have an average size ranging from 5 nm to 50 μm.

73. A composition according to claim 72, wherein said additional solid particles have an average size ranging from 20 nm to 50 μm.

74. A composition according to claim 61, wherein said second additional solid particles comprise an amorphous material having a glass transition temperature of greater than or equal to 60° C.

75. A composition according to claim 74, wherein said second additional solid particles comprise an amorphous material having a glass transition temperature of greater than or equal to 80° C.

76. A composition according to claim 75, wherein said second additional solid particles comprise an amorphous material having a glass transition temperature of greater than or equal to 100° C.

77. A composition according to claim 74, wherein said amorphous material is a polymer.

78. A composition according to claim 77, wherein said polymer is chosen from ethylene polymers, propylene polymers, acrylic polymers, acrylamide polymers, methacrylonitrile polymers, polycarbonates, polyurethanes, polyesters, polyamides, polysulfones, polysulfonamides and carbohydrates.

79. A composition according to claim 74, wherein said second additional solid particles have an average size ranging from 10 nm to 50 μm.

80. A composition according to claim 79, wherein said second additional solid particles have an average size from 20 nm to 1 μm.

81. A composition according to claim 61, wherein said third additional solid particles comprise a wax having a hardness 6.5 MPa to 20 MPa.

82. A composition according to 81, wherein said wax is chosen from candelilla wax, hydrogenated jojoba wax, sumac wax, ceresin, octacosanyl stearate, tetracontanyl stearate, shellac wax, behenyl fumarate, bis(1,1,1-trimethylolpropane)tetrastearate, bis(1,1,1-trimethylolpropane)tetrasteabehenate, ozokerites, the wax obtained by hydrogenation of olive oil esterified with stearyl alcohol, and the waxes obtained by hydrogenation of castor oil esterified with cetyl alcohol.

83. A composition according to claim 82, wherein said third additional solid particles comprise a wax having a hardness from 9.5 MPa to 15 MPa.

84. A composition according to claim 61, further comprising auxiliary particles other than said rigid phase of said multiphase particles and said additional solid particles, said auxiliary particles not being capable of coalescing at a temperature below 40° C.

85. A composition according to claim 1, comprising a volatile fraction, a nonvolatile fraction comprising solid particles chosen from multiphase particles, additional solid particles and auxiliary solid particles, said solid particles being present in a content such that the volume fraction of said solid particles is greater than or equal to 50% of the total volume of the nonvolatile fraction of said composition.

86. A composition according to claim 1, comprising a volatile fraction, a nonvolatile fraction comprising solid particles chosen from multiphase particles, additional solid particles and auxiliary solid particles, said solid particles being present in a content such that the volume fraction of said solid particles is from 50% to 99% of the total volume of the nonvolatile fraction of said composition.

87. A composition according to claim 1, comprising a volatile fraction, a nonvolatile fraction comprising solid particles chosen from multiphase particles, additional solid particles and auxiliary solid particles, said solid particles being present in a content such that the volume fraction of said solid particles is greater than or equal to 60% of the total volume of the nonvolatile fraction of said composition.

88. A composition according to claim 1, comprising a volatile fraction, a nonvolatile fraction comprising solid particles chosen from multiphase particles, additional solid particles and auxiliary solid particles, said solid particles being present in a content such that the volume fraction of said solid particles is from 60% to 99% of the total volume of the nonvolatile fraction of said composition.

89. A composition according to claim 1, comprising a volatile fraction, a nonvolatile fraction comprising solid particles chosen from multiphase particles, additional solid particles and auxiliary solid particles, said solid particles being present in a content such that the volume fraction of said solid particles is greater than or equal to 70% of the total volume of the nonvolatile fraction of said composition.

90. A composition according to claim 1, comprising a volatile fraction, a nonvolatile fraction comprising solid particles chosen from multiphase particles, additional solid particles and auxiliary solid particles, said solid particles being present in a content such that the volume fraction of said solid particles is from 70% to 95% of the total volume of the nonvolatile fraction of said composition.

91. A composition according to claim 61, comprising a volatile fraction, a nonvolatile fraction comprising solid particles chosen from multiphase particles, additional solid particles and auxiliary solid particles, and said rigid phases of said multiphase particles and said first additional solid particles are present in the composition in a content such that the volume fraction of said rigid phases of said multiphase particles and of said first additional particles is between 10% and 90% of the total volume of the fraction of solid particles.

92. A composition according to claim 1, comprising a volatile fraction and a nonvolatile fraction comprising said multiphase particles, said rigid phases of said multiphase particles being present in the composition in a content such that the volume fraction of said rigid phases of said multiphase particles is between 0.55% and 99% of the total volume of the nonvolatile fraction of the composition.

93. A composition according to claim 1, comprising a volatile fraction and a nonvolatile fraction comprising said multiphase particles, said rigid phases of said multiphase particles being present in the composition in a content such that the volume fraction of said rigid phases of said multiphase particles is between 1% and 95% of the total volume of the nonvolatile fraction of the composition.

94. A composition according to claim 1, comprising a volatile fraction and a nonvolatile fraction comprising said multiphase particles, said rigid phases of said multiphase particles being present in the composition in a content such that the volume fraction of said rigid phases of said multiphase particles is between 10% and 70% of the total volume of the nonvolatile fraction of the composition.

95. A composition according to claim 61, further comprising an additional wax.

96. A composition according to claim 1, further comprising an additional film-forming polymer.

97. A composition according to claim 96, wherein said additional film-forming polymer is a polymer capable of forming a deposit, especially a film, producing, at a concentration of 7% in water, a shrinkage of isolated stratum corneum of greater than 1% at 30° C. under a relative humidity of 40%.

98. A composition according to claim 97, wherein said additional film-forming polymer is a polymer capable of forming a deposit, especially a film, producing, at a concentration of 7% in water, a shrinkage of isolated stratum corneum of greater than 1.2% at 30° C. under a relative humidity of 40%.

99. A composition according to claim 98, wherein said additional film-forming polymer is a polymer capable of forming a deposit, especially a film, producing, at a concentration of 7% in water, a shrinkage of isolated stratum corneum of greater than 1.5% at 30° C. under a relative humidity of 40%.

100. A composition according to claim 1, further comprising an emulsifying surfactant.

101. A composition according to claim 1, wherein said composition is in a form chosen from wax-in-water, water-in-wax, oil-in-water and water-in-oil emulsions and anhydrous compositions.

102. A composition according to claim 1, further comprising at least one additive chosen from pigments, nacres, fillers, plasticizers, coalescers, vitamins, trace elements, softeners, sequestering agents, fragrances, oils, thickeners, proteins, ceramides, plasticizers, cohesion agents, acidifying or basifying agents, fillers, pigments, emollients and preserving agents.

103. A composition according to claim 1, wherein said composition is a mascara.

104. A process for coating keratin fibers, comprising applying to said keratin fibers a composition comprising a dispersion of multiphase particles in a cosmetically acceptable medium, said multiphase particles comprising at least one at least partially external supple phase comprising at least one supple polymer having at least one glass transition temperature of less than or equal to 60° C. and at least one at least partially internal rigid phase, said rigid phase being an amorphous material having at least one glass transition temperature of greater than 60° C., said at least one supple polymer being at least partially attached by chemical grafting onto said rigid phase.

105. A process according to claim 104, wherein said keratin fibers are eyelashes.

106. A process for curling eyelashes, said process comprising applying to said fibers a composition comprising a dispersion of multiphase particles in a cosmetically acceptable medium, said multiphase particles comprising at least one at least partially external supple phase comprising at least one supple polymer having at least one glass transition temperature of less than or equal to 60° C. and at least one at least partially internal rigid phase, said rigid phase being an amorphous material having at least one glass transition temperature of greater than 60° C., said at least one supple polymer being at least partially attached by chemical grafting onto said rigid phase.

107. A process for curling eyelashes, comprising applying to the eyelashes a mascara composition comprising multiphase particles dispersed in a cosmetically acceptable medium, said particles comprising at least one at least partly internal supple phase comprising at least one supple polymer having at least one glass transition temperature of less than or equal to 60° C., and at least one at least partly external rigid phase, said rigid phase being an amorphous material having at least one glass transition temperature of greater than 60° C., said supple polymer being at least partially attached by chemical grafting onto said rigid phase.

* * * * *

UNITED STATES PATENT AND TRADEMARK OFFICE
CERTIFICATE OF CORRECTION

PATENT NO.   : 6,793,940 B2
DATED        : September 21, 2004
INVENTOR(S)  : Florence Tournilhac et al.

It is certified that error appears in the above-identified patent and that said Letters Patent is hereby corrected as shown below:

Column 20,
Line 34, "bands." should read -- bonds. --.

Column 21,
Line 42, "according to 39," should read -- according to claim 39, --.

Column 23,
Line 8, "according to claim claim 62," should read -- according to claim 62, --.
Line 11, "according to claim claim 65," should read -- according to claim 65, --.
Lines 52-53, "methacrylonitrile" should read -- (meth)acrylonitrile --.
Line 64, after "hardness", insert -- from --.
Line 65, "according to 81," should read -- according to claim 81, --.

Signed and Sealed this

First Day of February, 2005

JON W. DUDAS
*Director of the United States Patent and Trademark Office*